United States Patent
Runci et al.

(10) Patent No.: US 11,442,139 B2
(45) Date of Patent: *Sep. 13, 2022

(54) CLINIC WAIT-TIME VISIBILITY AND RESERVATIONS

(71) Applicant: CVS Pharmacy, Inc., Woonsocket, RI (US)

(72) Inventors: Lisa Marie Runci, Mendon, MA (US); Kathryn Gillmeister, North Grafton, MA (US); James Dyson, IV, Glocester, RI (US)

(73) Assignee: CVS Pharmacy, Inc., Woonsocket, RI (US)

( * ) Notice: Subject to any disclaimer, the term of this patent is extended or adjusted under 35 U.S.C. 154(b) by 158 days.

This patent is subject to a terminal disclaimer.

(21) Appl. No.: 16/915,186

(22) Filed: Jun. 29, 2020

(65) Prior Publication Data
US 2020/0326406 A1    Oct. 15, 2020

Related U.S. Application Data

(63) Continuation of application No. 14/961,111, filed on Dec. 7, 2015, now Pat. No. 10,698,078.

(51) Int. Cl.
*G16H 40/20* (2018.01)
*G01S 5/10* (2006.01)

(52) U.S. Cl.
CPC .............. *G01S 5/10* (2013.01); *G16H 40/20* (2018.01)

(58) Field of Classification Search
CPC ........ G16H 40/20; G16H 10/60; G06Q 10/02; G06Q 10/06314; G06F 19/325
See application file for complete search history.

(56) References Cited

U.S. PATENT DOCUMENTS

| | | | |
|---|---|---|---|
| 3,859,511 A * | 1/1975 | Walker | G06C 3/00 235/85 R |
| 4,237,344 A | 12/1980 | Moore | |
| 7,249,036 B2 | 7/2007 | Bayne | |
| 7,668,732 B1 * | 2/2010 | Charles | G16H 40/20 705/2 |
| 7,684,998 B1 * | 3/2010 | Charles | G16H 50/20 705/2 |
| 8,504,291 B2 | 8/2013 | Bayne | |
| 8,751,255 B2 | 6/2014 | Brown | |
| 8,758,238 B2 | 6/2014 | Clapp | |
| 8,831,963 B2 | 9/2014 | Backer et al. | |
| 8,852,093 B2 | 10/2014 | Clapp et al. | |
| 9,646,135 B2 | 5/2017 | Pecora | |
| 9,734,288 B2 | 8/2017 | Pecora | |
| 2007/0136118 A1 | 6/2007 | Gerlach et al. | |
| 2009/0204449 A1 | 8/2009 | Waytena et al. | |
| 2010/0017216 A1 | 1/2010 | Chakra et al. | |
| 2010/0017222 A1 | 1/2010 | Yeluri et al. | |
| 2011/0224998 A1 | 9/2011 | Schoenberg | |
| 2011/0307547 A1 | 12/2011 | Backer et al. | |
| 2012/0158934 A1 | 6/2012 | Xiao et al. | |
| 2012/0166218 A1 | 6/2012 | Reiner | |

(Continued)

*Primary Examiner* — Reginald R Reyes
(74) *Attorney, Agent, or Firm* — Patent Law Works LLP (57) ABSTRACT

A plurality of clinics proximate a physical location of a client device of a user is identified, and wait-time information is transmitted to the client device. The user of the client selects one of the plurality of clinics, and a position in the customer queue of the clinic is reserved.

20 Claims, 8 Drawing Sheets

(56) References Cited

U.S. PATENT DOCUMENTS

| | | |
|---|---|---|
| 2013/0304534 A1 | 11/2013 | Mehta et al. |
| 2016/0063194 A1 | 3/2016 | Cao |
| 2016/0148121 A1 | 5/2016 | Durham et al. |
| 2016/0253464 A1 | 9/2016 | Balwani et al. |
| 2016/0321548 A1 | 11/2016 | Ziskind et al. |
| 2017/0124526 A1 | 5/2017 | Sanderford et al. |
| 2017/0185721 A1 | 6/2017 | Schuck |
| 2018/0046768 A1 | 2/2018 | Paskett |
| 2018/0158555 A1 | 6/2018 | Cashman et al. |

* cited by examiner

CLINIC WAIT-TIME VISIBILITY AND RESERVATIONS

CROSS-REFERENCE TO RELATED APPLICATIONS

The present application is a continuation of U.S. patent application Ser. No. 14/961,111, titled "Clinic Wait-Time Visibility and Reservations," and filed on Dec. 7, 2015, the content of which is hereby incorporated by reference in its entirety.

TECHNICAL FIELD

Embodiments of the present invention relate generally to appointment scheduling and, more particularly, to systems and methods for reserving appointments at one or more medical clinics.

BACKGROUND

When a person needs health care from a medical professional, such as a doctor, nurse, nurse practitioner, physician assistant, or pharmacist, he or she may not have the time or ability to schedule an appointment with and/or travel to the medical professional. The person may not be able to leave their place of work during a time at which the medical professional is available, for example, or may not be able to leave his or her children or other family members who are in need of supervision long enough to travel to the medical professional. In other cases, the health care that the person requires is so urgent that he or she cannot afford the time to travel to the medical professional; the medical professional may further not be available for an appointment soon enough. In still other cases, the reason for the health care, while still important to the person, may not rise to a level sufficient to warrant the time and expense of a doctor visit.

In response to these issues, some pharmacies offer in-store clinics at which people may request health care from an in-store medical professional, such as a nurse practitioner or physician assistant. The clinics, in some cases, do not require a pre-arranged appointment; the person may simply walk into the pharmacy and request medical care. The convenience and accessibility of these in-store clinics may help people have access to health care or advice that they otherwise would not have, as well as help reduce overall health-care costs by shifting some care away from the formality and expense of a full-blown doctor visit to a much more efficient consultation with an in-store medical professional.

The popularity of these clinics presents a problem, however: a person may arrive at a pharmacy hoping to speak to a medical professional only to find that one or more other people are already waiting for the same thing, and the person may not have enough time to wait. The clinic could attempt to address this problem by requiring or allowing people to schedule appointments with the in-store medical professionals, but scheduling appointments may run contrary to the walk-in convenience of the clinics and ultimately deter customers from seeking help. A need therefore exists for a system and method for managing walk-in medical clinic wait times.

SUMMARY

Embodiments of the present invention include systems and methods for providing clinic wait-time visibility and reservations. A user of a client device, such as a smartphone, tablet computer, laptop computer, or any other type of client device, activates a software application configured to execute on the client device. The software application communicates with a remote server computer to identify a plurality of medical clinics proximate a physical location of the client device. The server and/or one or more clinics receives wait-time information from each of the plurality of clinics indicating an associated wait time for a next available appointment at each clinic. The server and/or one or more clinics thereafter transmits a message to the client device identifying each clinic and associated wait time. The user selects one of the clinics, and, based on the selection, the client software application transmits the selection from the client device to the server and/or clinic. The selected clinic then enters the user into a position in a customer queue for that clinic.

In one aspect, a system for providing clinic wait-time visibility and reservations includes a network interface configured for communication with a client device of a user; a non-volatile computer memory for storing wait-time information associated with a plurality of clinics; and a computer processor configured for executing software instructions to identify a plurality of clinics proximate a physical location of the client device of the user; receive wait-time information from each of the plurality of clinics indicating an associated wait time for each clinic; electronically transmit a message to the client device of the user over the network interface identifying each clinic and associated wait time; receive, in response to the message, a selection from the client device of the user for one clinic in the plurality of clinics; and electronically transmit the selection to the one clinic for entry into a position in a customer queue of the one clinic.

The computer processor may be further configured for executing software instructions to transmit real-time updates of the wait time associated with the one clinic to the client device and/or for executing software instructions to receive identification information of the user from the client device and to transmit the received identification information to the one clinic. The identification information may include a first name, last name, date of birth, ZIP code, email address, or phone number; the client device may be a smartphone, tablet computer, laptop computer, desktop computer, or in-store kiosk. The computer processor may be further configured for executing software instructions to calculate a travel time from the physical location of the client device to each of the plurality of clinics and to transmit the travel times to the client device, for executing software instructions to monitor a location of the client device and adjust the position in the customer queue if the client device is not in or near the one clinic when the associated wait time elapses, for executing software instructions to monitor a trajectory of the client device and adjust the position in the customer queue if the client device is not due to be in or near the one clinic when the associated wait time elapses, and/or for executing software instructions to electronically transmit a message to the client device if a clinic other than the one clinic has a shorter wait time.

In another aspect, a method for providing clinic wait-time visibility and reservations includes identifying a plurality of clinics proximate a physical location of a client device of a user; receiving wait-time information from each of the plurality of clinics indicating an associated wait time for each clinic; electronically transmitting a message to the client device of the user over the network interface identifying each clinic and associated wait time; receiving, in response to the message, a selection from the client device of the user for one clinic in the plurality of clinics; and electronically transmitting the selection to the one clinic for entry into a position in a customer queue of the one clinic.

Real-time updates of the wait time associated with the one clinic may be transmitted to the client device. Identification information of the user (e.g., a first name, last name, date of birth, ZIP code, email address, or phone number) may be received from the client device and transmitting the received identification information to the one clinic. The client device may be a smartphone, tablet computer, laptop computer, desktop computer, or in-store kiosk. A travel time from the physical location of the client device to each of the plurality of clinics may be calculated and transmitted to the client device. A location of the client device may be monitored and the position in the customer queue may be adjusted if the client device is not in or near the one clinic when the associated wait time elapses. A trajectory of the client device may be monitored and the position in the customer queue may be adjusted if the client device is not due to be in or near the one clinic when the associated wait time elapses. A message may be transmitted to the client device if a clinic other than the one clinic has a shorter wait time.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

Various embodiments of the present invention include systems and methods for providing clinic wait-time visibility and reservations. A user of a client device, such as a smartphone, tablet computer, laptop computer, or any other type of client device, activates a software application configured to execute on the client device. The software application communicates with a remote server computer to identify a plurality of medical clinics proximate a physical location of the client device. The server and/or one or more clinics receives wait-time information from each of the plurality of clinics indicating an associated wait time for a next available appointment at each clinic. The server and/or one or more clinics thereafter transmits a message to the client device identifying each clinic and associated wait time. The user selects one of the clinics, and, based on the selection, the client software application transmits the selection from the client device to the server and/or clinic. The selected clinic then enters the user into a position in a customer queue for that clinic.

Figure 1:
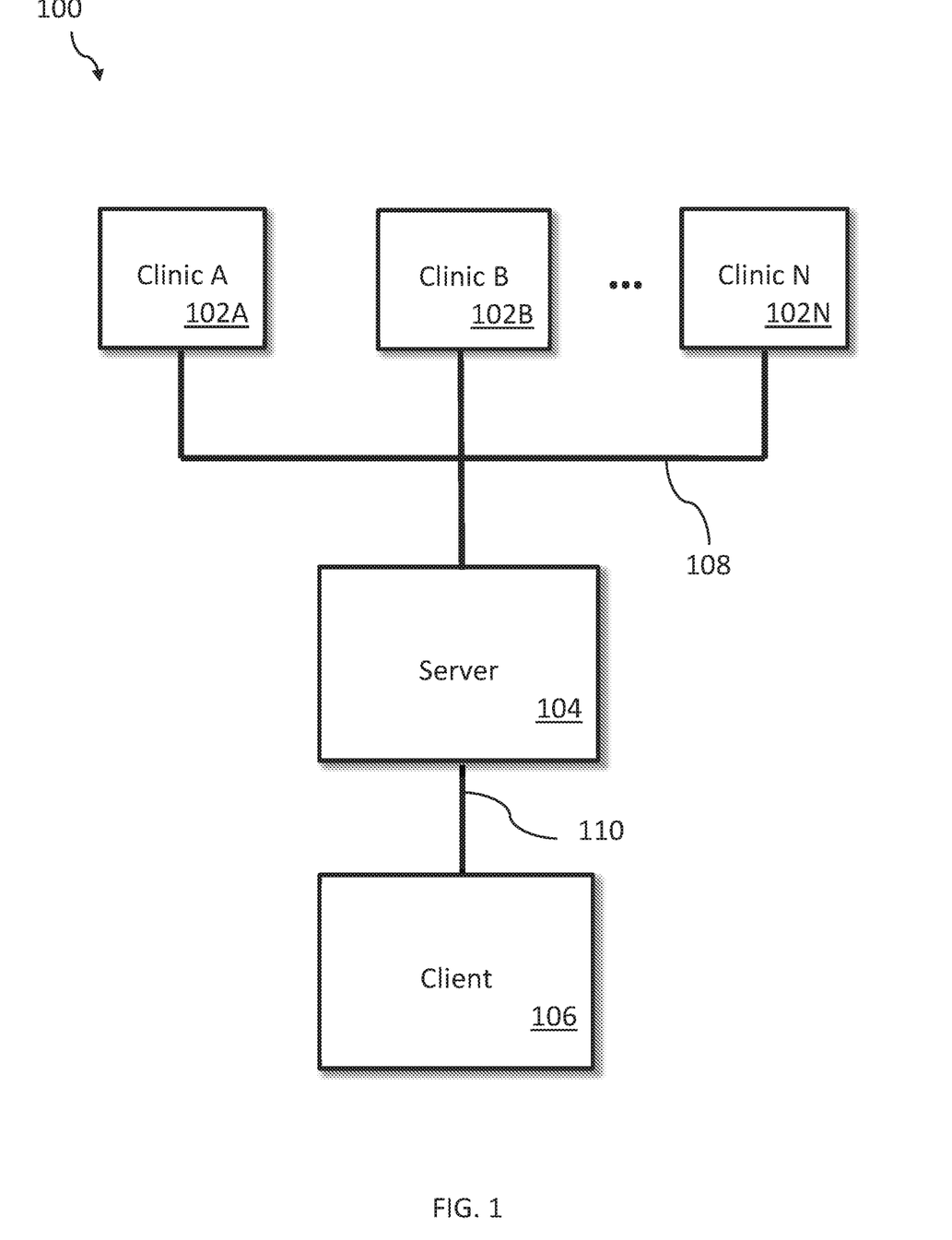
FIGS. 1 and 2 illustrate exemplary computing environments that include systems for providing clinic wait-time visibility and reservations in accordance with embodiments of the present invention.

FIG. 1 illustrates a computing environment 100 that includes a plurality of clinic computers 102A, 102B, . . . 102N, a server computer 104, and a client computer 106. The clinic computers 102A, 102B, . . . 102N (collectively referred to herein as the clinic computers 102) may be any type of desktop computer, workstation computer, laptop computer, handheld computer, point-of-sale system, etc., and they may be physically disposed at any store, pharmacy, medical office, kiosk, or location that provides any kind of medical-consultation, diagnosis, or prescribing service. In some embodiments, the clinic computers 102 are disposed at kiosks or counters inside pharmacies and are operated by one or more clinic technicians and/or medical professionals. The clinic computers 102 may perform a variety of functions, such as entering patient information, confirming insurance information, etc.; in some embodiments, the clinic computers 102 instead or in addition maintain an electronic, first-in-first-out queue of people in the pharmacy who have requested to meet with the medical professional at the clinic but have not yet done so. The clinic technician may enter personal information into the client computer 102 when a person arrives at the clinic and requests to meet with a medical professional using a keyboard, touchscreen, or other input device, and the clinic computer 102 may thereafter associate an entry in the queue with the personal information related to that person. As people meet with the medical professional and their meetings conclude, the information associated with the people is removed from the queue, and the people next in the queue are seen. One of skill in the art will understand that any method of implementing such a queue is within the scope of the present invention.

The server computer 104 may be any type of server computer, such as an application server, web server, and/or file server, and may include a processor, storage, memory, etc. The server computer 104 may be a single physical device or a collection of devices connected together via a network or local interconnect. The server computer 104 may be a real (i.e., non-virtual) device dedicated to executing the systems and methods discussed herein (and, in some embodiments, other dedicated tasks), the server computer 104 may be a virtual, cloud-based device provided by a cloud-computing vendor, or the server computer 104 may be a mixture of dedicated and virtual devices. The server computer 104 is described in greater detail below.

The client computer 106 may be any type of personal computing device, such as a desktop or laptop computer, tablet computer, cellular telephone, personal-digital assistant, or any other type of similar device. The client computer 106 may include a processor, storage, memory, etc., as well as an input device (e.g., a keyboard, mouse, microphone, or touchscreen) and an output device (e.g., a screen, touchscreen, or speaker). The client computer 106 is described in greater detail below.

Figure 2:
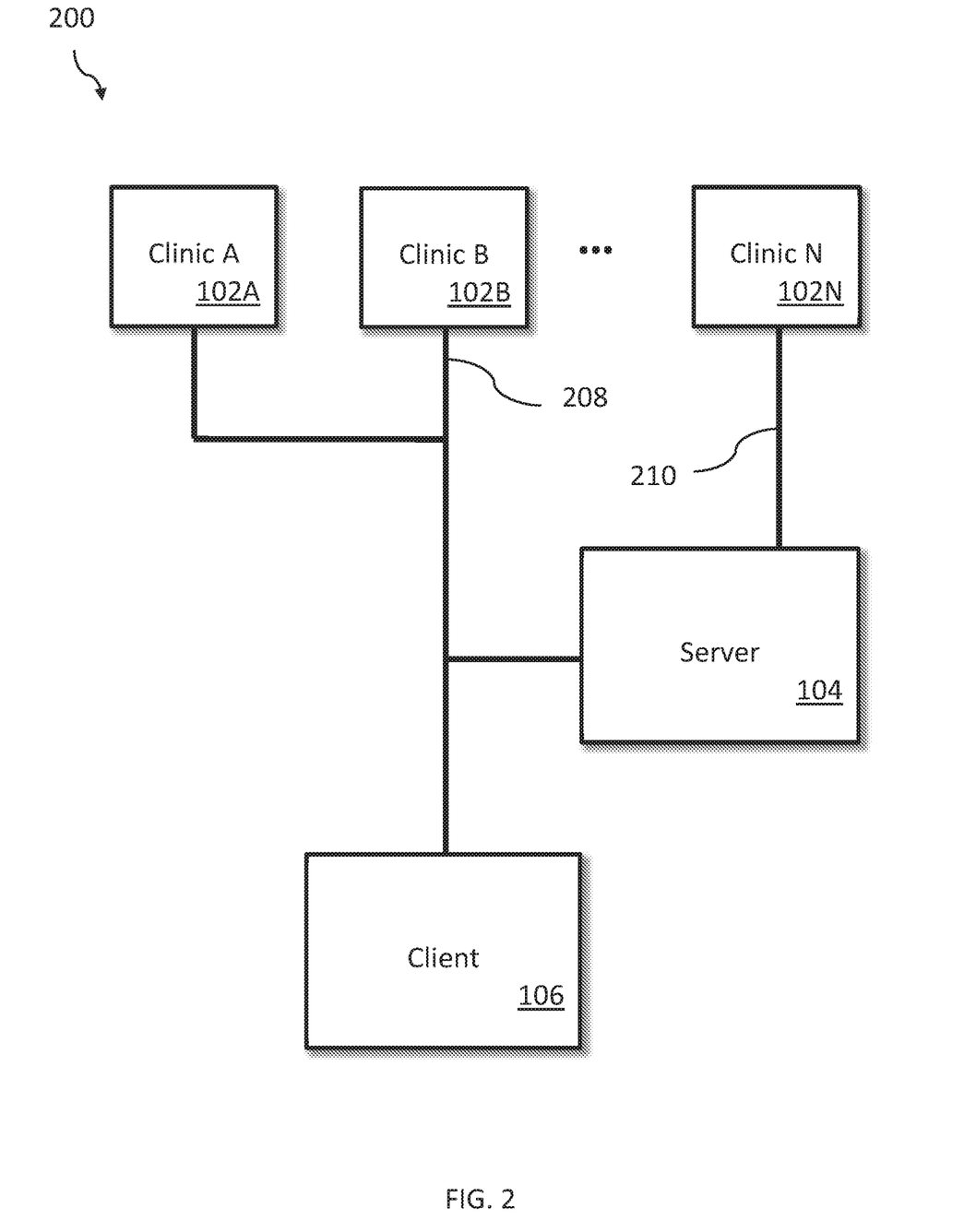

As shown in FIG. 1, the server computer 104 communicates with the clinic computers 102 via a network connection 108 and with the client computer 106 via a separate network connection 110. Alternatively, as shown in the computing environment 200 of FIG. 2, the clinics 102, server 104, and client 106 may communicate using the same network connection 208, while some other clinic computers 102 may communicate with the server computer 104 using a separate network connection 210. Any system of network connections is within the scope of the present invention, however. The network connections 108, 110, 208, 210 may be any network type known in the art, such as the Internet, private wide-area network, or local network, may be wired or wireless, and may use any type of network protocol, such as Ethernet, Wi-Fi, cellular networks, Bluetooth, or any other protocol.

Figure 3:
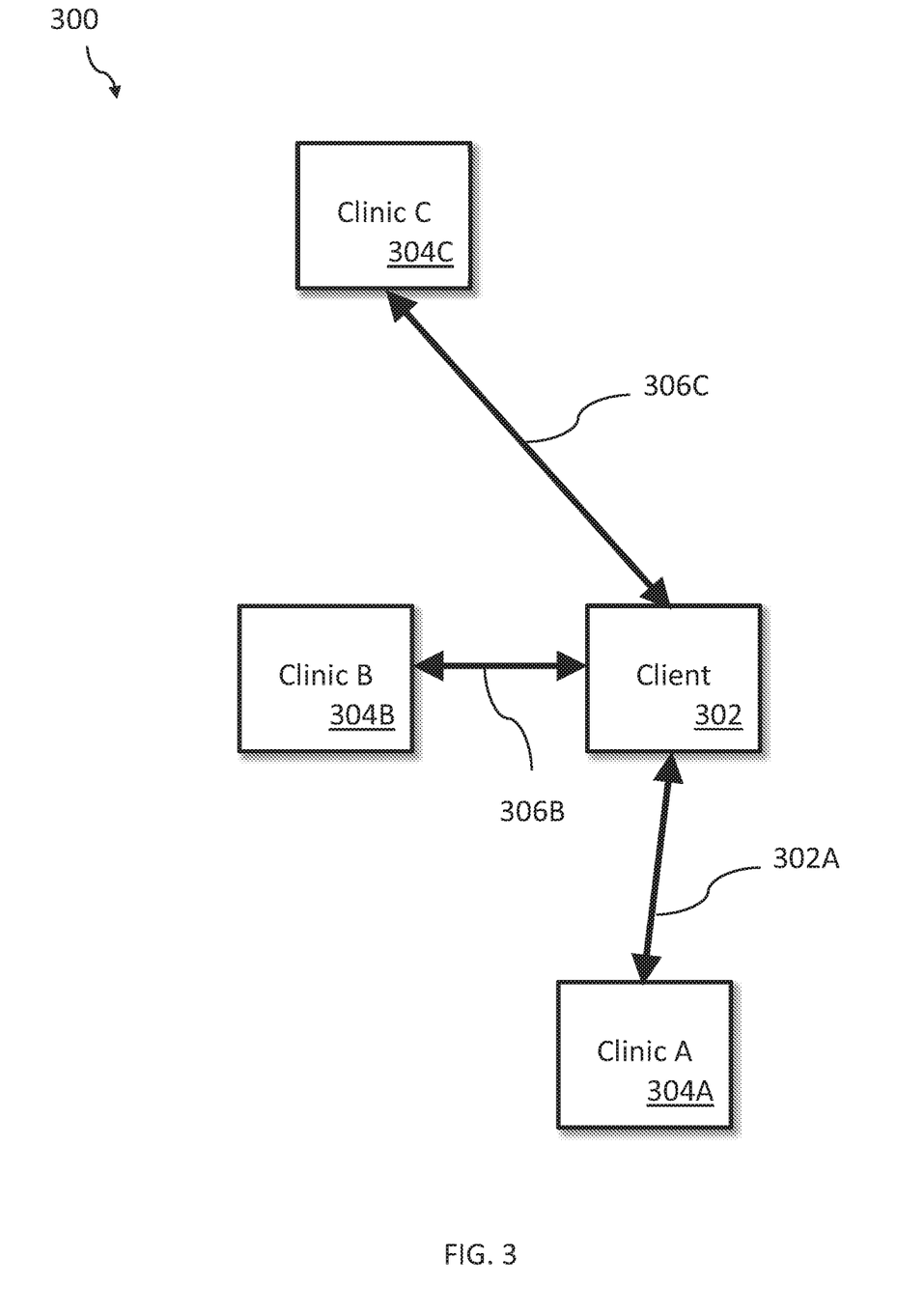
FIG. 3 illustrates an exemplary location of a client device with respect to various clinics in accordance with an embodiment of the present invention.

FIG. 3 illustrates an overhead view of an exemplary physical environment 300 that includes a client computer 302 and three clinic computers 304A, 304B, 304C. The client computer 302 is disposed at a first physical location and the three clinic computers 304A, 304B, 304C are disposed in three other physical locations and are separated in space from the client computer 302 by three different distances 306A, 306B, 306C. In this example, the distances 306A, 306B, 306C are shown as straight lines, but one of skill in the art will understand that real-world routes involving roads, paths, and other transportation features are within the scope of the present invention. As explained in greater detail below, a person may use the client computer 302 to determine a wait time at each of the clinics by communicating, either directly or via a server, with the three clinic computers 304A, 304B, 304C, select one of the three clinic computers 304A, 304B, 304C based on the wait times, and reserve a place in a queue at the selected one of the three clinic computers 304A, 304B, 304C.

Figure 4:
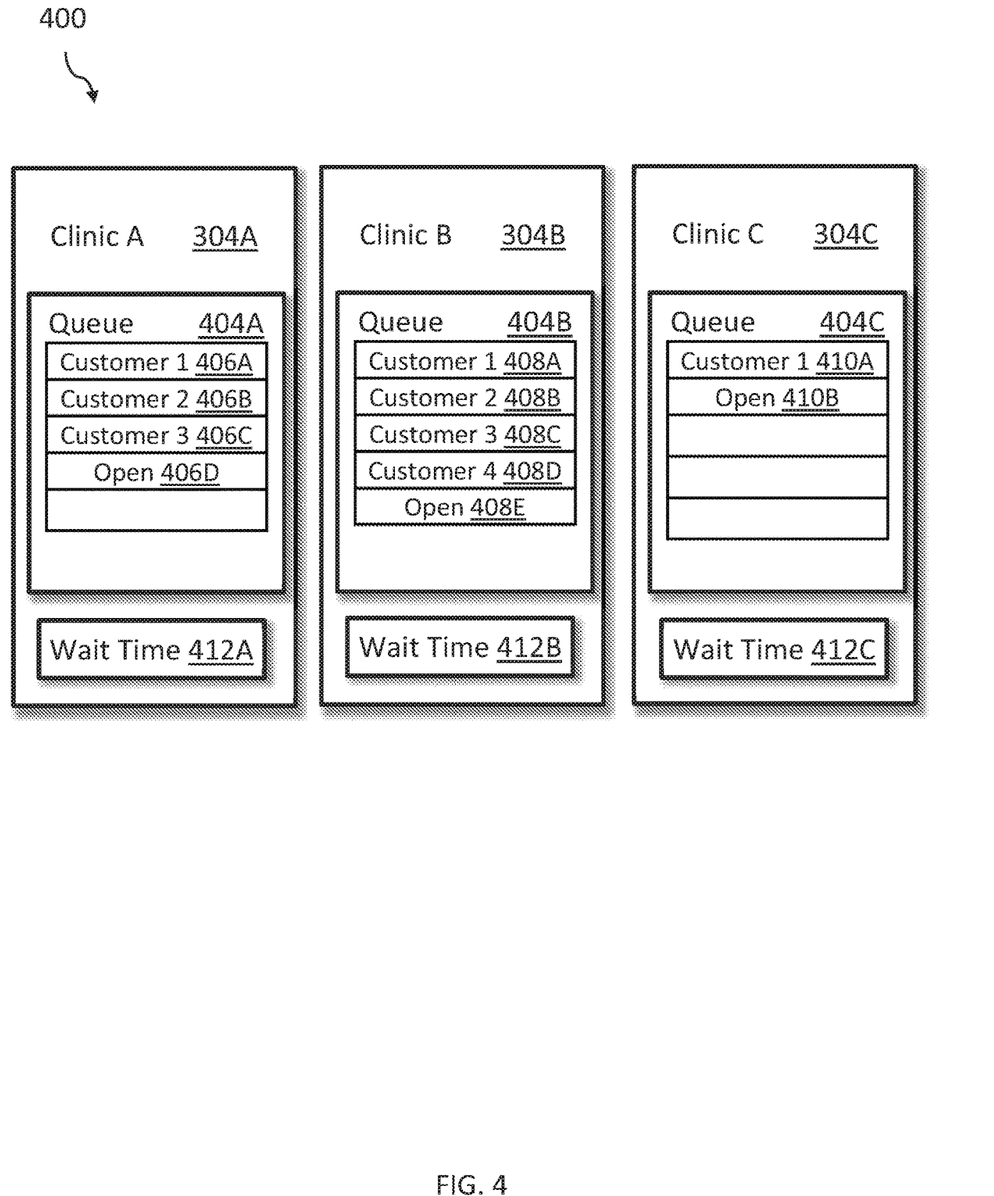
FIG. 4 illustrates exemplary wait-time queues in accordance with an embodiment of the present invention.

FIG. 4 illustrates an example 400 of data structures stored in three clinic computers 304A, 304B, 304C in accordance with embodiments of the present invention. Each clinic computer 304A, 304B, 304C includes a queue 404A, 404B, 404C that stores and maintains entries for each person waiting at the clinic corresponding to each clinic computer 304A, 304B, 304C. For example, a first queue 404A on a first clinic computer 304A contains three entries 406A, 406B, 406C corresponding to three waiting customers; a first customer 406A arrived first at the clinic and entered the queue 404A, followed by a second customer 406B and a third customer 406C. When a medical professional at the clinic with the first clinic computer 404A becomes available, the first customer 406A meets with the medical professional and is removed from the queue 404A. If one or more additional people arrive at the clinic and request to see the medical professional(s), they are added into the first open sloe 406D. The second queue 404B on the second clinic computer 304A, 304B, 304C has four entries 408A, 408B, 408C, 408D, and the third queue 404C on the third clinic computer 304C has one entry 410A.

Each clinic computer 304A, 304B, 304C further includes a wait time 412A, 412B, 412C that estimates how long it would take a person newly added to an open slot 406D, 408E, 410B to each queue 404A, 404B, 404C to see a medical professional at each clinic associated with each clinic computer 304A, 304B, 304C. The clinic computers 304A, 304B, 304C may estimate the wait time using any of a number of methods. In some embodiments, the clinic computers 304A, 304B, 304C multiply how long, on average, it takes for a medical professional to provide care to a person by the number of people waiting in the queues 404A, 404B, 404C. This average length of time may be set by an operator of a clinic computer 304A, 304B, 304C and/or by an operator of a server computer in communication with the clinic computers 304A, 304B, 304C; the average length of time may be the same for all clinic computers 304A, 304B, 304C or may vary for some or all clinic computers 304A, 304B, 304C.

In other embodiments, the average length of time is computed by the server and/or clinic computers 304A, 304B, 304C based on the lengths of time of some or all past clinic visits. For example, the length of time of visits with one or more medical professionals at one or more clinics may be collected over time by the clinic computers 304A, 304B, 304C, and these visit lengths may be averaged. The average length of time may be computed or re-computed once, from time to time, or on a periodic basis.

The predicted wait times 412A, 412B, 412C may be compared to actual wait times for each clinic visitor. If the predicted wait times 412A, 412B, 412C are consistently longer than the actual wait times, future predicted wait times 412A, 412B, 412C may be increased. If, on the other hand, the predicted wait times 412A, 412B, 412C are consistently shorter than the actual wait times, future predicted wait times 412A, 412B, 412C may be decreased.

The predicted wait times 412A, 412B, 412C may vary based on a time of day, day of week, and/or week or month of year of clinic visits. For example, the server and/or clinic computers 304A, 304B, 304C may observe that clinic visits take longer, on average, in the mornings than in the afternoons (or vice versa) or take longer, on average, on certain days of the week compared to others, and adjust the predicted wait times 412A, 412B, 412C accordingly.

In some embodiments, the predicted wait times 412A, 412B, 412C for a person newly added to an open slot 406D, 408E, 410B vary based on the types of visit for the people ahead of the newly added person in each queue 404A, 404B, 406C. A reason for each clinic visit for each person may be entered into the clinic computers 304A, 304B, 304C when each person arrives at the clinic and requests to see a medical professional; the reason may be a specific medical condition or question or a general category of condition or question. If the reason is predicted to not take much time for the medical professional to answer or address, the length of time of visit for the requester is decreased, on the other hand, if the reason is predicted to be complicated and will take longer for the medical professional to answer or address, the length of time of visit for the requester is increased. The current predicted wait time 412A, 412B, 412C for a newly arrived person is then determined by adding together the estimated length of time of visit of each person in the queue ahead of the new arrival. For example, if each person in the queue ahead of the new arrival is there only for a flu shot, the wait time may be short (e.g., 2-3 minutes per person in the queue ahead of the new arrival). If, on the other hand, if each person in the queue ahead of the new arrival is there for a potential diagnosis of a potentially complicated ailment, the wait time may be long (e.g., 10-15 minutes per person in the queue ahead of the new arrival).

In some embodiments, the wait times 412A, 412B, 412C are updated for each person in a queue when better predictions are available. Better predictions may be made available when a person ahead of other people in the queue completes his or her clinic visit and/or runs over a predicted time, and the time of completion or run-over differs from a predicted time of completion by a noticeable amount (e.g., 1 minute, 3 minutes, 5 minutes, or longer). If, for example, a current visit was predicted to take 15 minutes but instead finishes in 10 minutes, the estimated wait times for people already in the queue, as well as the wait time for a new visit request, decreases by 5 minutes. Similarly, if a current visit was predicted to take 15 minutes but instead finishes in 20 minutes and/or is still ongoing at 20 minutes, the estimated wait times for people already in the queue, as well as the wait time for a new visit request, increases by 5 minutes.

Figure 5:
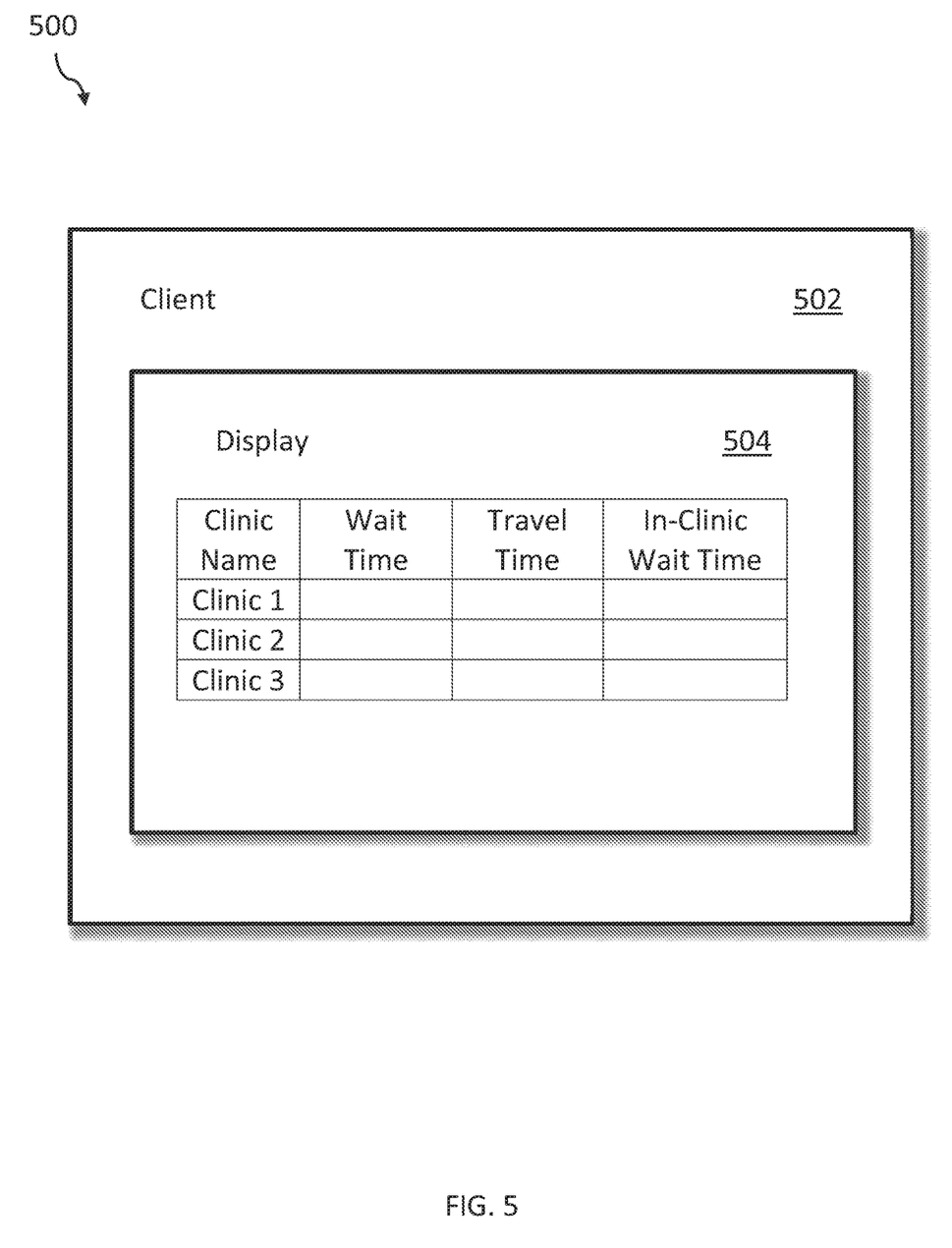
FIG. 5 illustrates an exemplary client device display in accordance with an embodiment of the present invention.

FIG. 5 illustrates a client computer 500 having a housing 502 and a user interface 504 (e.g., a display). One of skill in the art will understand that the client computer 500 may contain or include other features, such as buttons, keys, speakers, etc. not shown in FIG. 5. As mentioned above, the client computer 500 executes a client software application that permits a user to locate clinics, view wait times of clinics, select a clinic, reserve a spot in a queue at a clinic, and/or perform other functions described herein. The client software application may be a stand-alone application, such as an application downloaded from a website or app store, a web page loaded in a web browser, or any other type of application. The user interface 504 is only an example of a user interface that the client software application may display; one of skill in the art will understand that many different styles of user interfaces are within the scope of the present invention.

In various embodiments, the display 504 includes one or more clinic names and associated wait times for each clinic. When the user launches the client software application and/or activates a user-interface control of the client software application, one or more clinics proximate the client computer are identified. In various embodiments, the location of the client computer is determined by using a global-positioning-system signal received from one or more satellites, by using a cellular signal broadcast from one or more cellular transmitters, or by any other means known in the art. In some embodiments, the operating system executing on the client computer 500 provides a location-management service that returns the location of the client computer 500 upon request (using, for example, an application-programming interface). In other embodiments, the user inputs his or her location manually (by, for example, entering an address, city name, or ZIP code into the client computer 500).

Using the location of the client computer 500 and a list or map of known clinic locations, the client computer 500 may identify one or more clinics physically near the client computer 500. In some embodiments, the client computer 500 transmits its location to a remote computer, such as a server computer, which identifies the clinics and transmits them back to the client computer 500. In other embodiments, the client computer 500 includes a list of clinics and their locations and identifies the nearby clinics without communicating with the server computer. The clinics may be selected if they are within a certain distance to the client computer 500 (e.g., ten miles), if they are within a certain travel time from the client computer 500 (e.g., twenty minutes), if the user of the client computer 500 has indicated that a clinic is a preferred clinic, or by other such criteria. If more than a certain number (e.g., five or ten) of clinics meet the criteria, only a closest subset of the clinics may be displayed on the client computer 500. In some embodiments, if the user enters location information such as a city name or ZIP code, some or all of the clinics in that city or ZIP code are displayed.

Each clinic further transmits an estimated wait time that represents an amount of time the user would have to wait if he or she were physically present at the clinic and requested entry into that clinic's queue. The wait times may be transmitted directly from the clinic computers to the client computer or transmitted to the server computer and then to the client computer. Each wait time may be displayed on the display 504 as a number of minutes, the time that the user would be able to see the medical professional, as a bar or line graph, or any other such visual means.

In some embodiments, the wait time may include the time it would take the user to travel to the clinic as well as the in-clinic wait time. A nearby clinic may have a long in-clinic wait time, for example, while a distant clinic has a short or no in-clinic wait time; the user may prefer to travel farther to a clinic in order to take advantage of the shorter in-clinic wait time. The travel time may be estimated using any means known in the art, such as by calculating a route from the user to the clinic and estimating a rate of travel on the route given the type of streets that make up the route, current traffic, etc.

The user selects a clinic given the displayed list of clinics and associated wait times by interacting with the client computer 500 using any input device, such as a keyboard, mouse, touchscreen, or microphone. The client computer 500 then transmits the selection to the associated clinic computer (in some embodiments, via a server computer) along with information identifying the client computer 500 and/or user. In some embodiments, the client software application collects information from the user such as his or her name, username, email address, street address, doctor name, insurance information, etc., and transmits some or all of this information to the clinic computer. The information may be collected from the user when the clinic selection is made, when the client software application is launched, or as part of a user-account creation process. Instead of or in addition to the information identifying the user, the client computer 500 may transmit information identifying itself, such as its IP or MAC address.

The selected clinic computer enters the user into its queue upon receipt of the selection and may send a message confirming the entry to the client computer 500. The client computer 500 may thereafter display the wait time on the display 504, which may change as time passes. The client software application may alert the user when the wait time approaches ten minutes, five minutes, or zero by displaying an alert on the display 504, vibrating, or playing a sound.

The server computer and/or clinic computers may transmit wait-time updates to the client computer 500 if and when the wait time changes due to factors other than the mere passage of time. If, for example, a person ahead of the user in the queue takes a longer or shorter amount of time with the medical professional than predicted, the server computer and/or clinic computer may transmit an update to the client 500 that adjusts the wait time accordingly. Other reasons for transmitting an update to the client computer 500 include one or more other people in the queue canceling their request to see the medical professional, arrival or departure of medical professionals at the clinic, or any other such reason.

In some embodiments, the client computer 500 displays the wait times of a plurality of clinics on the display 504 even after the user has selected one clinic and has been entered into that clinic's queue. The user may choose to transfer his or her request to see a medical professional at the selected clinic and enter the queue in another clinic. The user may choose to make this transfer if, for example, the wait time at the selected clinic increased, the wait time at another clinic decreased, or for any other reason. In some embodiments, if another clinic experiences a drop in its wait time, the server computer and/or clinic computer transmits a message to the client computer 500 informing the user of this drop and offering for the user to select the other clinic. The user may be entered into the new queue at the end or at a position having a wait time that most closely corresponds to the wait time of the user in the first queue.

In some embodiments, the server computer and/or clinic computers monitors the physical position of the client device 500 before, during, and/or after the user has selected a clinic. If the client device 500 is not in the selected clinic or not on a trajectory to arrive at the selected clinic when the wait time expires, the server computer and/or clinic computer may move the user's position in the queue back one or more positions (or, in some embodiments, remove the user from the queue entirely). The server computer and/or clinic computers may transmit a message to the client device 500 information the user of the movement and/or cancellation.

Figure 6:
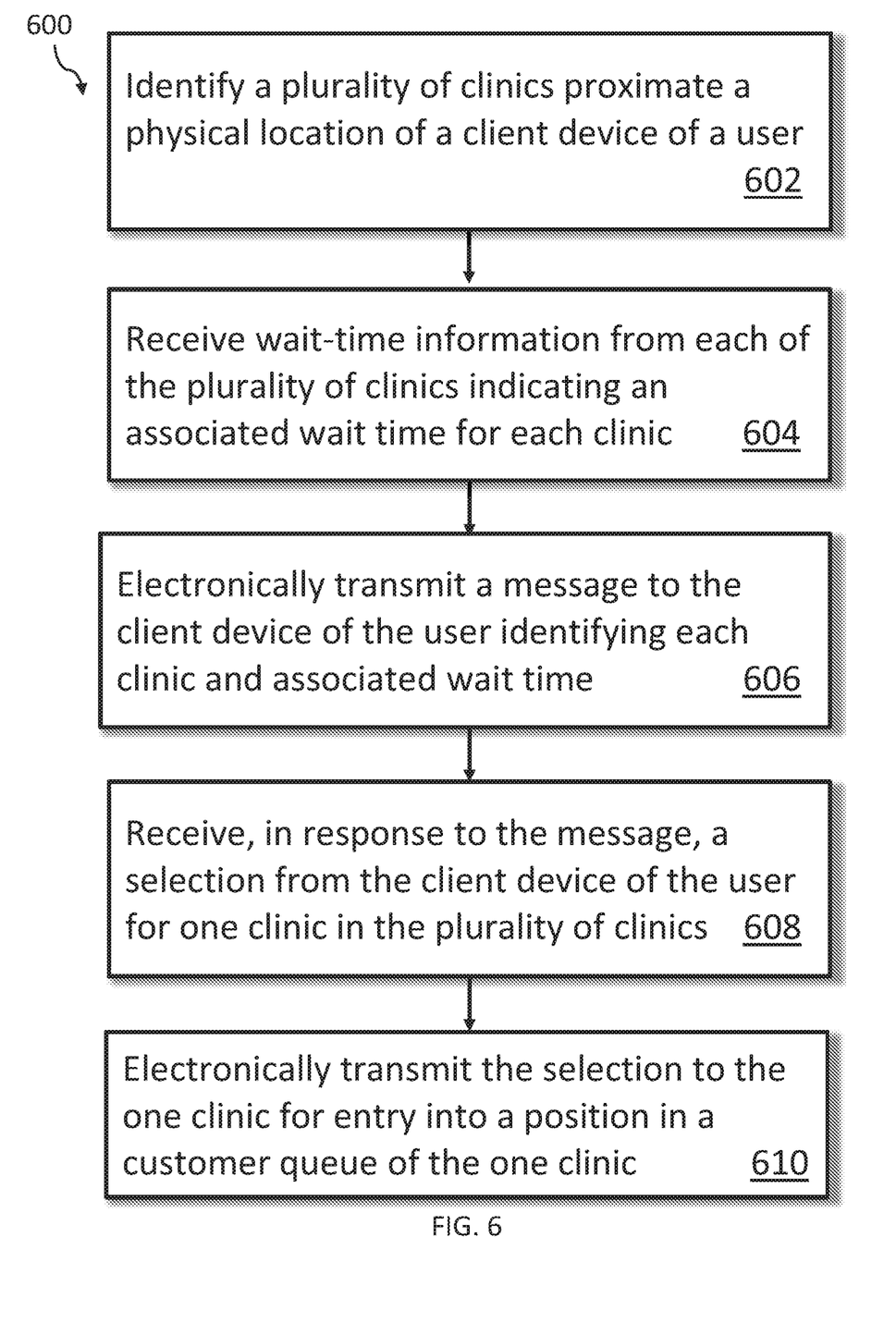
FIG. 6 illustrates a method for providing clinic wait-time visibility and reservations in accordance with embodiments of the present invention.

FIG. 6 illustrates a method 600 in accordance with embodiments of the present invention. In a first step 600, a plurality of clinics proximate a physical location of the client device of the user is identified. In a second step 604, wait-time information from each of the plurality of clinics indicating an associated wait time for each clinic is received. In a third step 606, a message is electronically transmitted to the client device of the user over the network interface identifying each clinic and associated wait time. In a fourth step 608, a selection from the client device of the user for one clinic in the plurality of clinics is received in response to the message. In a fifth step 610, the selection is electronically transmitted to the one clinic for entry into a position in a customer queue of the one clinic.

Figure 7:
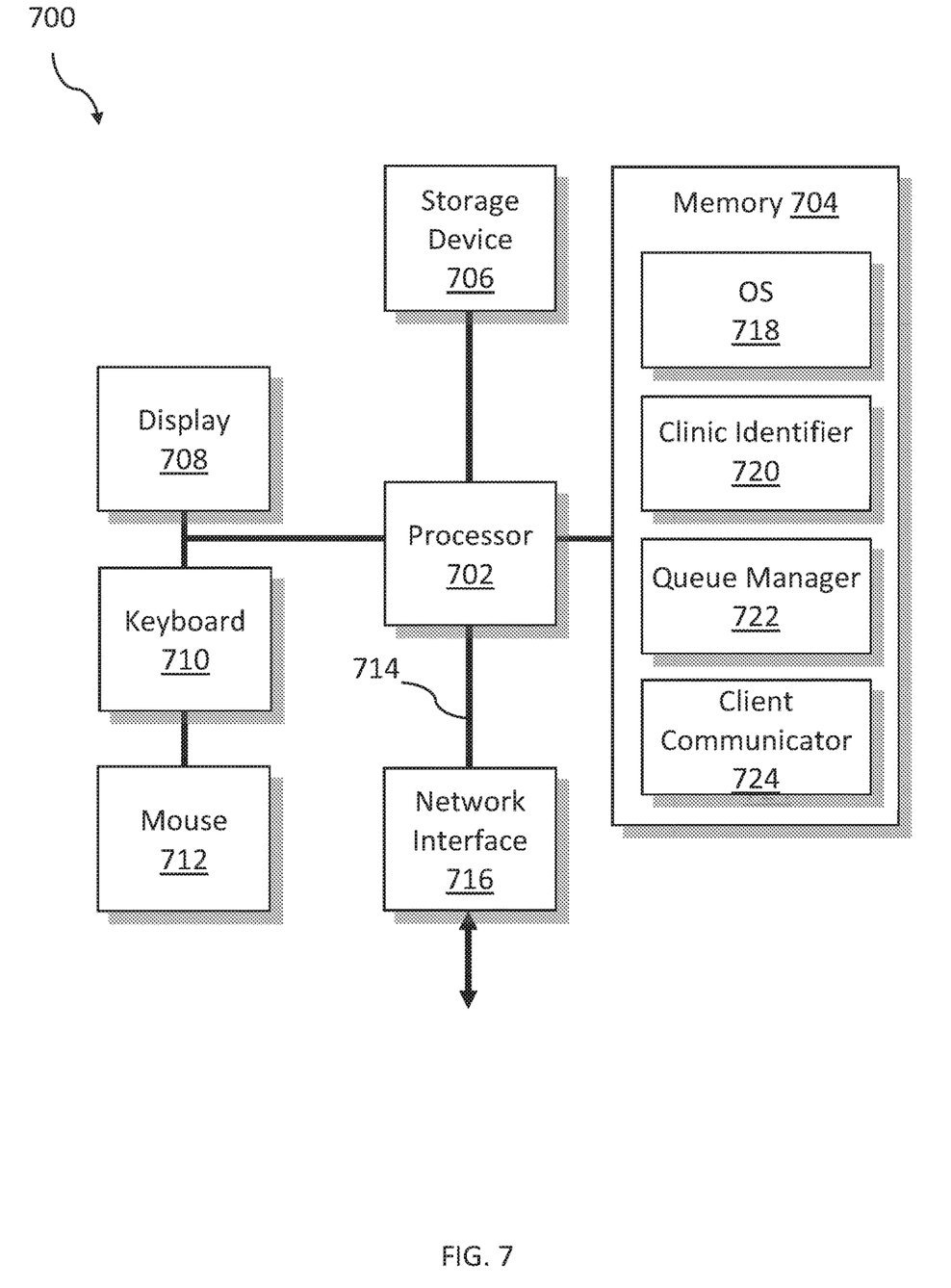
FIG. 7 illustrates an exemplary server and/or clinic computing device in accordance with an embodiment of the present invention.

FIG. 7 is a simplified block diagram of a suitably programmed general-purpose server 700 implementing embodiments of the present invention; the server 700 may be the server computer and/or clinic computer described above. The server 700 includes a processor 702 having one or more central processing units (CPUs), volatile and/or non-volatile main memory 704 (e.g., RAM, ROM, or flash memory), one or more mass storage devices 706 (e.g., hard disks, or removable media such as CDs, DVDs, USB flash drives, etc.), a display device 708 (e.g., a liquid-crystal display touchscreen or monitor), user-input devices such as a keyboard 710 and a mouse 712, and one or more buses 714 (e.g., a single system bus shared between all components or separate memory and peripheral buses) that facilitate communication between these components. A network interface 716 (e.g., a Wi-Fi or ETHERNET port) may be used to connect the server 700 to the Internet or other network.

The main memory 704 may be used to store instructions to be executed by the processor 702, conceptually illustrated as a group of modules. These modules generally include an operating system 718 (e.g., a Microsoft WINDOWS, Linux, or APPLE OS X operating system) that directs the execution of low-level, basic system functions (such as memory allocation, file management, and the operation of mass storage devices), as well as higher-level software applications, such as a clinic identifier 720 for identifying clinics proximate a client device, a queue manager 722 for managing one or more clinic queues, and a client communicator for sending and receiving messages to and from a client device. The various modules may be programmed in any suitable programming language, including, without limitation, high-level languages such as C, C++, Java, Perl, Python, or Ruby or low-level assembly languages. The memory 704 may further store input and/or output data associated with execution of the instructions as well as additional information used by the various software applications.

The server 700 is described herein with reference to particular blocks, but this description is not intended to limit the invention to a particular physical arrangement of distinct component parts. The server 700 is an illustrative example; variations and modifications are possible. The server 700 may be implemented in a variety of form factors, including server systems, desktop systems, cloud-based computers, etc. A particular implementation may include other functionality not described herein, e.g., wired and/or wireless network interfaces, media playing and/or recording capability, etc. Further, the computer processor may be a general-purpose microprocessor, but depending on implementation can alternatively be, e.g., a microcontroller, peripheral integrated circuit element, a customer-specific integrated circuit, an application-specific integrated circuit, a logic circuit, a digital signal processor, a programmable logic device such as a field-programmable gate array, a programmable logic device, a programmable-logic array, smart chip, or other device or arrangement of devices.

Figure 8:
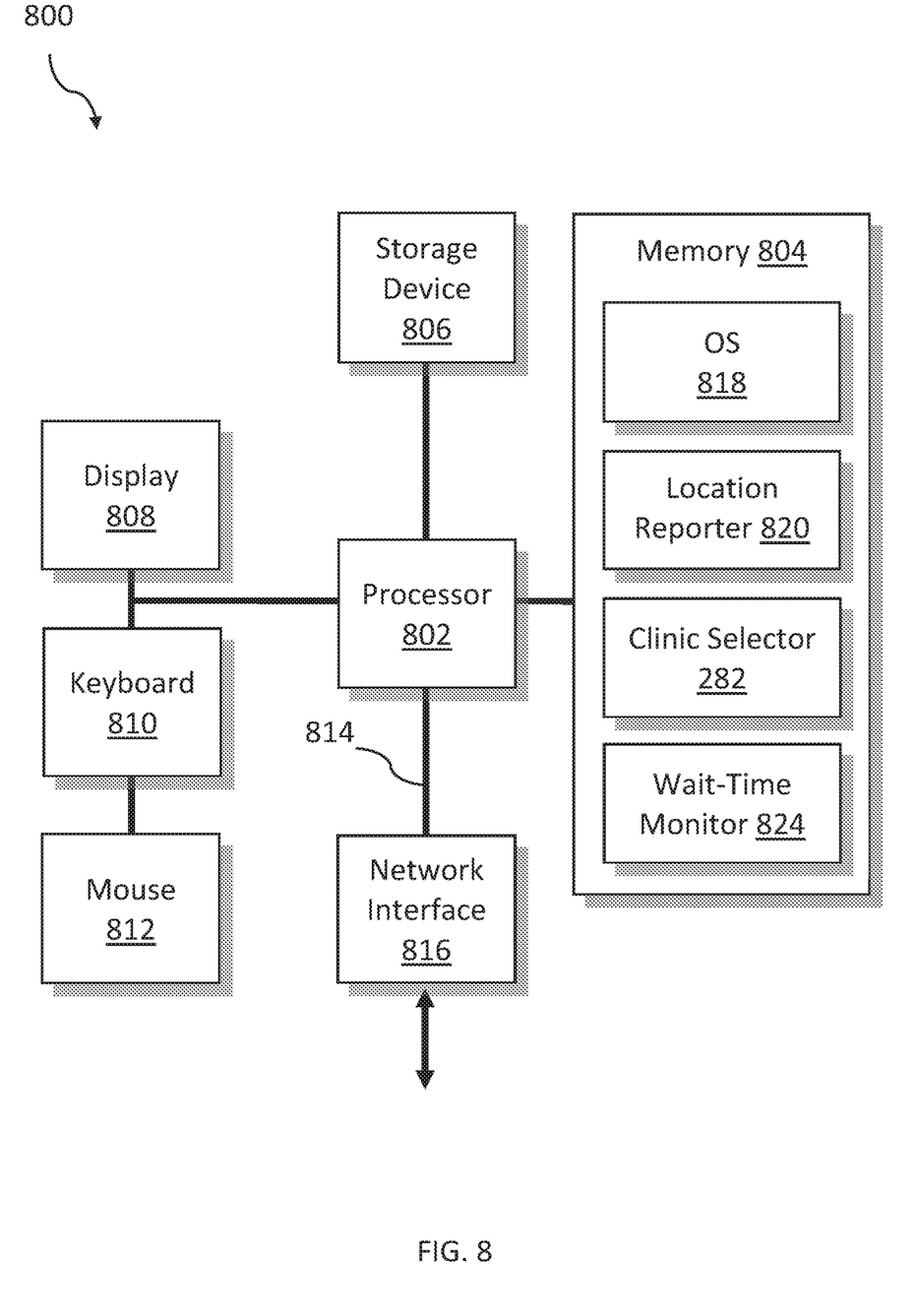
FIG. 8 illustrates an exemplary client computing device in accordance with an embodiment of the present invention.

FIG. 8 is a simplified block diagram of a suitably programmed client computer 800 implementing embodiments of the present invention. The client computer 800 includes a processor 802 having one or more central processing units (CPUs), volatile and/or non-volatile main memory 804 (e.g., RAM, ROM, or flash memory), one or more mass storage devices 786 (e.g., hard disks, or removable media such as CDs, DVDs, USB flash drives, etc.), a display device 808 (e.g., a liquid-crystal display touchscreen or monitor), user-input devices such as a keyboard 810 and a mouse 812, and one or more buses 814 (e.g., a single system bus shared between all components or separate memory and peripheral buses) that facilitate communication between these components. A network interface 816 (e.g., a Wi-Fi or ETHERNET port) may be used to connect the client computer 800 to the Internet or other network.

The main memory 804 may be used to store instructions to be executed by the processor 802, conceptually illustrated as a group of modules. These modules generally include an operating system 818 (e.g., an ANDROID or APPLE IOS operating system) that directs the execution of low-level, basic system functions (such as memory allocation, file management, and the operation of mass storage devices), as well as higher-level software applications, such as a location reporter 820 for determining a location of the client device, a clinic selector 822 for displaying clinics and wait times to the user and receiving a selection therefrom, and a wait-time monitor for displaying and updating wait times. The various modules may be programmed in any suitable programming language, including, without limitation, high-level languages such as C, C++, Java, Perl, Python, or Ruby or low-level assembly languages. The memory 804 may further store input and/or output data associated with execution of the instructions as well as additional information used by the various software applications.

The client computer 800 is described herein with reference to particular blocks, but this description is not intended to limit the invention to a particular physical arrangement of distinct component parts. The client computer 800 is an illustrative example; variations and modifications are possible. The client computer 800 may be implemented in a variety of form factors, including server systems, desktop systems, cloud-based computers, etc. A particular implementation may include other functionality not described herein, e.g., wired and/or wireless network interfaces, media playing and/or recording capability, etc. Further, the computer processor may be a general-purpose microprocessor, but depending on implementation can alternatively be, e.g., a microcontroller, peripheral integrated circuit element, a customer-specific integrated circuit, an application-specific integrated circuit, a logic circuit, a digital signal processor, a programmable logic device such as a field-programmable gate array, a programmable logic device, a programmable-logic array, smart chip, or other device or arrangement of devices.

It should also be noted that embodiments of the present invention may be provided as one or more computer-readable programs embodied on or in one or more articles of manufacture. The article of manufacture may be any suitable hardware apparatus, such as, for example, a floppy disk, a hard disk, an optical disk, a solid-state disk, a flash memory card, read-only or random-access memory, or a magnetic tape. In general, the computer-readable programs may be implemented in any programming language. Some examples of languages that may be used include C, C++, or JAVA. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system, comprising:
   a network interface configured for communication with a client device of a user;
   a non-volatile computer memory for storing wait time information indicating an associated wait time for each clinic of a plurality of clinics; and
   a computer processor configured for executing software instructions to launch a client application installed on the client device when the user requests health care, and, in response to the launch of the client application, to:
   receive a requested time when the user requests health care;
   generate and transmit to the client device to display on a user interface of the client application a first message identifying each clinic of the plurality of clinics and respective wait times around the requested time;
   receive from the client device a first selection from the user for a first clinic of the plurality of clinics;
   transmit the first selection to the first clinic for entry into a position in a first customer queue of the first clinic;
   monitor a location of the client device in real-time using a broadcast signal received by the client device;
   in response to the location of the client device, automatically update the wait time information for the user as displayed to the user interface of the client application;
   in response to the location of the user indicating the client device of the user is not near the first clinic when the wait time for the user in the first customer queue elapses, adjust the position of the user in the first customer queue of the first clinic and update the wait time information for the user;
   in response to a second clinic of the plurality of clinics having a shorter wait time than the updated wait time, automatically generate and transmit a second message identifying the second clinic to the user through the user interface of the client application so that the user has immediate access to the updated wait time information for updating the selection to the second clinic; and
   in response to a second selection from the user for the second clinic of the plurality of clinics, automatically transmit the second selection to the second clinic for entry into a position in a second customer queue of the second clinic.

2. The system of claim 1, wherein the computer processor is further configured, in response to the second selection, to automatically remove the user from the first customer queue of the first clinic.

3. The system of claim 1, wherein the computer processor is further configured to transmit real-time updates of the wait time associated with the first clinic to the user interface of the client device.

4. The system of claim 1, wherein the computer processor is further configured:
   to receive identification information of the user from the client device; and
   in response to the user being in the first customer queue of the first clinic, to transmit the received identification information of the user to the first clinic.

5. The system of claim 4, wherein the identification information comprises a first name, last name, date of birth, ZIP code, email address, or phone number.

6. The system of claim 1, wherein the client device comprises a smartphone, tablet computer, laptop computer, desktop computer, or in-store kiosk.

7. The system of claim 1, wherein the computer processor is further configured to calculate a travel time from the location of the client device to each of the plurality of clinics and to transmit the travel times to the user interface of the client device.

8. The system of claim 1, wherein the computer processor is further configured to monitor a trajectory of the client device and adjust the position in the first customer queue in response to the client device not being due to be in or near the first clinic when the wait time for the user in the first customer queue elapses.

9. The system of claim 1, wherein the plurality of clinics and respective wait times in the first message are provided as graphs for display in the user interface of the client device.

10. A method, comprising:
    receiving from a client application on a client device a requested time when a user requests health care;
    generating and transmitting to the client device to display on a user interface of the client application a first message identifying each clinic of a plurality of clinics and wait time information indicating an associated wait time for each clinic of a plurality of clinics occurring around the requested time;
    receiving from the client device a first selection from the user for a first clinic of the plurality of clinics;
    transmitting the first selection to the first clinic for entry into a position in a first customer queue of the first clinic;

monitoring a location of the client device in real-time using a broadcast signal received by the client device;

in response to the location of the client device, automatically updating the wait time information for the user as displayed to the user interface of the client application;

in response to the location of the user indicating the client device of the user is not near the first clinic when the wait time elapses, adjusting the position of the user in the first customer queue of the first clinic and update the wait time information for the user;

in response to a second clinic of the plurality of clinics having a shorter wait time than the updated wait time, automatically generating and transmitting a second message identifying the second clinic to the user through the user interface of the client application so that the user has immediate access to the updated wait time information for updating the selection to the second clinic; and in response to a second selection from the user for the second clinic of the plurality of clinics, automatically transmitting the second selection to the second clinic for entry into a position in a second customer queue of the second clinic.

11. The method of claim 10, further comprising automatically removing the user from the first customer queue of the first clinic in response to the second selection.

12. The method of claim 10, further comprising transmitting real-time updates of the wait time associated with the first clinic to the user interface of the client device.

13. The method of claim 10, further comprising:
receiving identification information of the user from the client device; and
transmitting the received identification information of the user to the first clinic in response to the user being in the first customer queue of the first clinic.

14. The method of claim 13, wherein the identification information comprises a first name, last name, date of birth, ZIP code, email address, or phone number.

15. The method of claim 10, wherein the client device comprises a smartphone, tablet computer, laptop computer, desktop computer, or in-store kiosk.

16. The method of claim 10, further comprising calculating a travel time from the location of the client device to each of the plurality of clinics and to transmit the travel times to the user interface of the client device.

17. The method of claim 10, further comprising:
monitoring a trajectory of the client device; and
adjusting the position in the first customer queue in response to the client device not being due to be in or near the first clinic when the wait time for the user in the first customer queue elapses.

18. The method of claim 10, further comprising providing the plurality of clinics and respective wait times in the first message as graphs for display in the user interface of the client device.

19. A system, comprising:
means for receiving from a client application on a client device a requested time when a user requests health care;
means for generating and transmitting to the client device to display on a user interface of the client application a first message identifying each clinic of a plurality of clinics and wait time information indicating an associated wait time for each clinic of a plurality of clinics occurring around the requested time;
means for receiving from the client device a first selection from the user for a first clinic of the plurality of clinics;
means for transmitting the first selection to the first clinic for entry into a position in a first customer queue of the first clinic;
means for monitoring a location of the client device in real-time using a broadcast signal received by the client device;
in response to the location of the client device, means for automatically updating the wait time information for the user as displayed to the user interface of the client application;
in response to the location of the user indicating the client device of the user is not near the first clinic when the wait time elapses, means for adjusting the position of the user in the first customer queue of the first clinic and update the wait time information for the user;
in response to a second clinic of the plurality of clinics having a shorter wait time than the updated wait time, means for automatically generating and transmitting a second message identifying the second clinic to the user through the user interface of the client application so that the user has immediate access to the updated wait time information for updating the selection to the second clinic; and
in response to a second selection from the user for the second clinic of the plurality of clinics, means for automatically transmitting the second selection to the second clinic for entry into a position in a second customer queue of the second clinic.

20. The system of claim 19, further comprising:
means for receiving identification information of the user from the client device; and
means for transmitting the received identification information of the user to the first clinic in response to the user being in the first customer queue of the first clinic.

* * * * *